(12) United States Patent
Cha et al.

(10) Patent No.: US 8,226,004 B2
(45) Date of Patent: Jul. 24, 2012

(54) BIOSENSOR MEASURING APPARATUS AND A METHOD THEREOF

(75) Inventors: Geun Sig Cha, Seoul (KR); Hakhyun Nam, Seoul (KR); Gang Cui, Seoul (KR); Keun-Ki Kim, Seoul (KR); Shim-Ho Lee, Seoul (KR)

(73) Assignee: i-SENS, Inc., Seoul (KR)

( * ) Notice: Subject to any disclaimer, the term of this patent is extended or adjusted under 35 U.S.C. 154(b) by 26 days.

(21) Appl. No.: 13/060,049

(22) PCT Filed: Nov. 11, 2008

(86) PCT No.: PCT/KR2008/006644
§ 371 (c)(1),
(2), (4) Date: Feb. 21, 2011

(87) PCT Pub. No.: WO2010/021429
PCT Pub. Date: Feb. 25, 2010

(65) Prior Publication Data
US 2011/0147457 A1    Jun. 23, 2011

(30) Foreign Application Priority Data
Aug. 22, 2008 (KR) .................. 10-2008-0082304

(51) Int. Cl.
*G06K 7/10* (2006.01)
(52) U.S. Cl. ............ 235/454; 235/435; 235/438
(58) Field of Classification Search .......... 235/435, 235/438, 439, 454, 462
See application file for complete search history.

(56) References Cited

U.S. PATENT DOCUMENTS

| 5,665,215 A | 9/1997 | Bussmann | |
|---|---|---|---|
| 7,819,320 B2 * | 10/2010 | Modavis et al. | 235/437 |
| 2003/0150724 A1 * | 8/2003 | Kawanaka et al. | 204/403.02 |
| 2005/0161323 A1 * | 7/2005 | Bae et al. | 204/403.01 |

FOREIGN PATENT DOCUMENTS

| JP | 06-229970 A | 8/1994 |
|---|---|---|
| KR | 10-2001-0022163 A | 3/2001 |
| KR | 10-0680267 B1 | 2/2007 |
| KR | 10-2008-0003419 A | 1/2008 |
| KR | 10-2008-0052349 | 6/2008 |

OTHER PUBLICATIONS

International Search Report prepared for the Korean Intellectual Property Office, dated Apr. 3, 2009, for International Application No. PCT/KR2008/006644.

* cited by examiner

*Primary Examiner* — Michael G Lee
*Assistant Examiner* — Matthew Mikels
(74) *Attorney, Agent, or Firm* — Sheridan Ross P.C.

(57) ABSTRACT

A biosensor can be measured by a method that includes: determining malfunction of a production lot information sensing unit; alerting malfunction when the production lot information sensing unit malfunctions; encoding the production lot information through the production lot information sensing unit when the production lot information sensing unit does not malfunction; and detecting a component of a sample through a biosensor strip by using the encoded production lot information.

19 Claims, 10 Drawing Sheets

BIOSENSOR MEASURING APPARATUS AND A METHOD THEREOF

CROSS REFERENCE TO RELATED APPLICATIONS

This application is a national stage application under 35 U.S.C. 371 of PCT Application No. PCT/KR2008/006644 filed 11 Nov. 2008, which designated the United States and which application claimed the benefit of Korean Application No. 10-2008-0082304, filed 22 Aug. 2008, the entire disclosures of which are incorporated by reference herein.

TECHNICAL FIELD

The present invention relates to an electrochemical biosensor measuring apparatus used with an electrochemical biosensor, and a measuring method thereof.

BACKGROUND ART

Recently, for the diagnosis and prophylaxis of diabetes mellitus, the importance of periodically monitoring blood glucose levels has been increasingly emphasized. Currently, strip-type biosensors designated to be used in hand-held portable measuring devices allows individuals to readily monitor glucose levels in the blood.

Many various commercially available biosensors measure the blood glucose content of blood samples using an electrochemical technique. The principle of the electrochemical technique is based on the following Reaction 1.

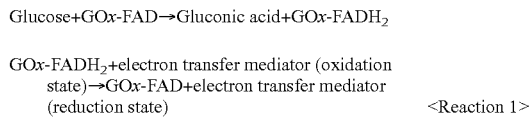

Glucose+GOx-FAD→Gluconic acid+GOx-FADH$_2$

GOx-FADH$_2$+electron transfer mediator (oxidation state)→GOx-FAD+electron transfer mediator (reduction state)   <Reaction 1>

In Reaction 1, GOx represents glucose oxidase, GOx-FAD and GOx-FADH$_2$ respectively represent an oxidized and a reduced state of glucose-associated FAD (flavin adenine dinucleotide), a cofactor required for the catalysis of glucose oxide.

For electron transfer mediators, the electrochemical biosensor uses organic electron transfer materials such as ferrocene, or ferrocene derivatives, quinones, quinone derivatives, organic or inorganic materials containing transition metals (hexamine ruthenium, polymers containing osmium, potassium ferricyanide, and the like), organic conductive salts, and viologens.

A principle of measuring the blood glucose level using the biosensor is as follows.

Glucose in the blood is oxidized to gluconic acid by the catalytic activity of glucose oxidase. In this case, the cofactor FAD of the glucose oxidase is reduced to FADH$_2$. The reduced FADH$_2$ transfers electron to the mediator, so that FADH$_2$ returns to its oxidized state and the mediator is reduced. The reduced mediator is diffused to the surface of the electrodes, and the concentration level of the glucose is measured by using a current generated by applying an oxidation potential of the electron transfer mediator in the reduced state in the surface of the working electrode. Compared to biosensors based on colorimetry, electrochemical biosensors have the advantages of not being influenced by oxygen and allowing the use of samples, even cloudy ones, without pretreatment thereof.

Although this electrochemical biosensor is generally convenient when used to monitor and control the amount of blood glucose, accuracy of the biosensor is greatly dependent on variation between respective mass-produced lots in which the biosensors are produced. In order to eliminate such variation, most of the commercialized biosensors are designed such that a user directly inputs calibration curve information that is predetermined at the factory into a measuring device that is capable of reading the biosensor. However, this method inconveniences the user, and leads to inaccurate results by allowing the user to make input errors.

In order to solve this problem, a method by which the resistance of each electrode can be adjusted such that production information for each lot is stored at the location at which contact of the electrode of a sensor occurs (US20060144704A1), a method in which a connection to a resistor bank is made (WO2007011569A2), and a method by which information is read by varying resistance through the adjustment of the length or the thickness of each electrode (US20050279647A1) have been proposed. The methods proposed for the electrochemical biosensors are all based on a technique for reading electrical variation. In addition, a method for distinguishing production lot information by reading the resistivity of a conductor marked on a strip using an electrical method (U.S. Pat. No. 4,714,874) has been proposed.

However, the above-proposed methods function to accurately adjust resistance, and require a process of mass-producing the sensors first, measuring the statistical characteristics of the sensors, and post-processing the measured information again using a method of adjusting the resistance marked on the sensors. Further, the process of accurately adjusting the resistance through the post-processing, when it is marked in large quantities, is very inconvenient and is difficult to use in practical application.

Methods in which colored marks are used with a spectral system that is capable of discriminating colors to realize a colorimetric method (U.S. Pat. No. 3,907,503, U.S. Pat. No. 5,597,532, U.S. Pat. No. 6,168,957), and methods that are capable of reading bar codes (EP00075223B1, WO02088739A1) have been proposed. These methods using color or bar codes are favorable for a colorimetric method-based sensor using the spectrum system, but they have technical and economic difficulties when applied to a system using an electrochemical measurement mechanism. For example, the size and structure of the area where the electrochemical sensor strip is inserted into the measuring device for the purpose of electrical connection, that is, the connection space of the sensor strip, is very limited when constructing a device and circuit for spectroscopically identifying a structure into which the production lot information is input, which results in a great increase in system construction expense.

In addition, instead of the methods of marking the production lot information on the sensor strip, a method of recording information on a container or pack containing a sensor and allowing the information to be read by the measuring device has been proposed. However, this method also has a possibility of allowing the user to make an error.

For conventional methods developed in order for users to measure the blood glucose levels thereof using disposable electrochemical biosensor strips without the need to manually input accurate calibration curve information about biosensors, which differ from one production lot to another, into a measuring device, the sensors require a long period of time for the preparation thereof, and also require post-processing in which errors are likely to be made.

Also, conventional devices for reading hue marks using a filter or a monochromator for the wavelength of a light source encounter spatial limitations and cause problems in the construction of small-sized systems.

Thus, there is a need for a biosensor that has a mark which is simple and can be easily marked within a short time period, such as hue marks, which are convenient to print on a small area of a biosensor, or hole marks, which can be easily prepared simultaneously when the final press process for mass production is performed, thereby allowing the biosensor to be produced on a mass scale. Also, there is a need for a biosensor that has production lot information recorded on the mark through which the production lot information can be thus inputted to an insulation plate of the biosensor, so that when the biosensor is inserted into a measuring device, the production lot information is automatically identified without a mistake being made by a user, thus enabling blood glucose to be conveniently and accurately measured and being economical.

However, when a part used for automatically encoding production lot information malfunctions, incorrect production lot information may be encoded. Therefore, if malfunction of a part for encoding production lot information is determined and malfunction of the part can be alerted, an error of relying on a biosensor measuring result that is calculated incorrectly based on incorrect encoded production lot information can be prevented. Further, a user of the biosensor measuring device can repair the biosensor measuring device or replace it with a new one. Such a function can be very helpful for a diabetes patient who needs to refer to an accurate biosensor measuring result.

DETAILED DESCRIPTION

Technical Problem

The present invention has been made in an effort to provide a measuring device that can automatically encode production lot information of a biosensor without allowing a mistake to be made by a user upon insertion of an electrochemical biosensor to thereby enable blood glucose to be conveniently and accurately measured, and that can determine malfunction of a part that may cause an encoding error of the production lot information to alert the malfunction of the part.

Technical Solution

An exemplary biosensor measuring method according to an embodiment of the present invention uses production lot information for detecting a component of a sample through a biosensor strip that is provided with a production lot information identification unit including at least one production lot information mark, and the production lot information is encoded by emitting light through a light emission unit and receiving light passed through the production lot information unit through a detection unit.

The biosensor measuring method may include: determining malfunction if a production lot information sensing unit malfunctions; alerting malfunction when the production lot information sensing unit malfunctions; encoding the production lot information through the production lot information sensing unit when the production lot information sensing unit does not malfunction; and detecting a component of a sample through the biosensor strip by using the encoded production lot information.

An exemplary biosensor measuring device according to an embodiment of the present invention detects a component of a sample through a biosensor strip provided with a production lot information identification unit that includes at least one production lot information mark, and the biosensor measuring device includes a production lot information sensing unit provided with a light emission unit and a detection unit and generates a production lot information signal based on light emitted from the light emission unit and passed through the production lot information identification unit; and a measuring module that encodes the production lot information based on the signal from the production lot information sensing unit and uses the encoded production lot information in sample component detection through the biosensor strip.

The measuring module may include at least one processor that is activated by a predetermined program, and the predetermined program may include a series of commands for performing the measuring method according to the exemplary embodiment of the present invention.

Advantageous Effects

As described above, the electrochemical biosensor measuring device and the measuring method thereof according to the exemplary embodiment of the present invention enables a user to conveniently use the biosensor measuring device by encoding a production lot information mark that has been marked on a biosensor without manually inputting production lot information of the biosensor into the measuring device.

In addition, the measuring device can be down-sized since it requires a very small area by using a plurality of hole marks, and an unused back side of the biosensor can be used.

In addition, malfunction of a sensing unit for encoding a production lot information mark is detected and alerted to a user, and therefore a medical hazard that can be caused by relying on an incorrect detected component measuring value can be prevented. Here, the medical hazard includes a case in which blood glucose level is measured to be normal even though it is not normal, so that necessary medical treatment cannot be provided.

BRIEF DESCRIPTION OF THE REFERENCE
NUMERALS OF THE DRAWINGS

| 104: electrode | 110: biosensor strip |
|---|---|
| 200: biosensor measuring device | 300: insertion unit |
| 400: measuring module | 410: button |
| 450: memory | 460: display window |
| 501, 502, 503, 504, 505: production lot information mark | |
| 510: transmission film | |
| 500: production lot information identification unit | |
| 700: sensor connector | 700a: connector body |
| 700b: sliding structure of connector | |
| 702: light emitter | 703: detector |
| 704: circuit substrate | 705: electrical connection unit |
| 706: transmission window | 707: image signal identification device |
| 720: light emission unit | 730: detection unit |
| 800: production lot information sensing unit | |

Best Mode

In the present specification, the term "biosensor" is used to have the same meaning as the term "biosensor strip".

Hereinafter, an exemplary embodiment of the present invention will be described in further detail.

Figure 1:
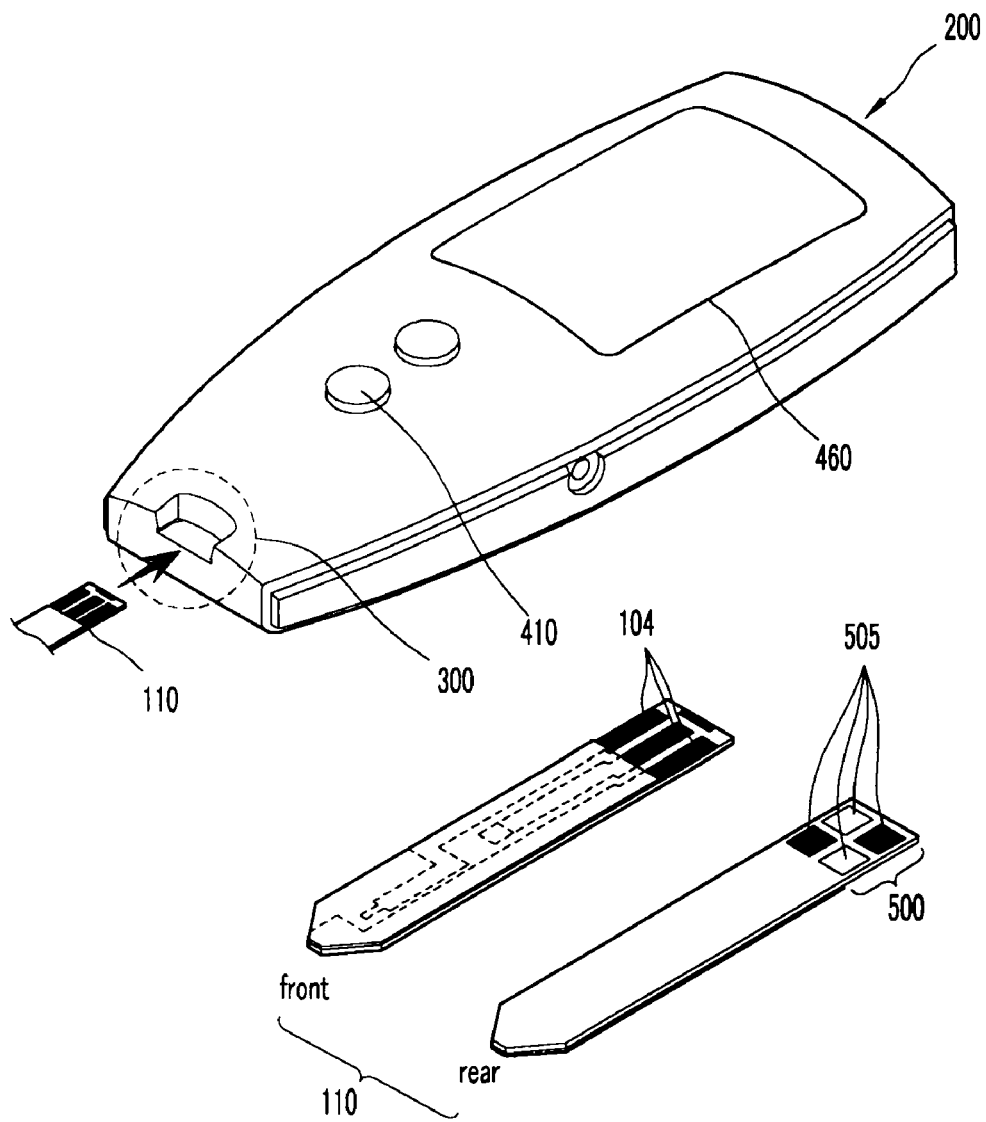
FIG. 1 shows a biosensor measuring device and a biosensor strip used therein according to an exemplary embodiment of the present invention.
Figure 2:
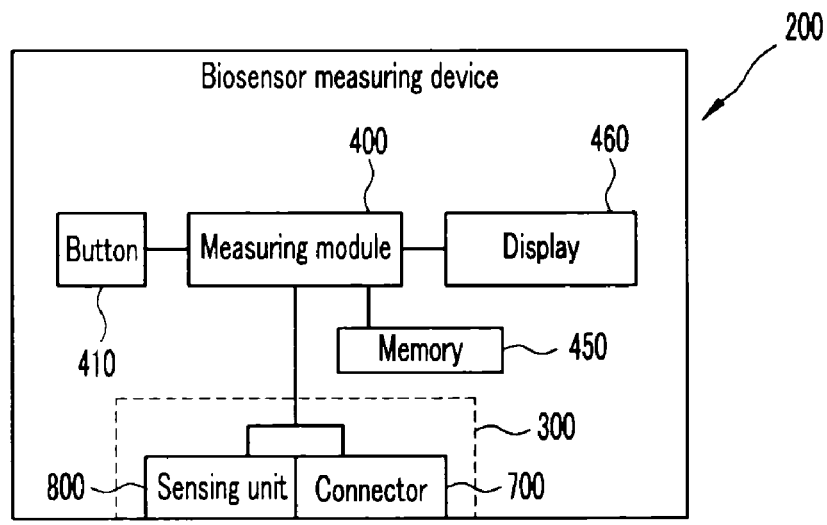
FIG. 2 is a block diagram of the biosensor measuring device according to the exemplary embodiment of the present invention.
Figure 10:
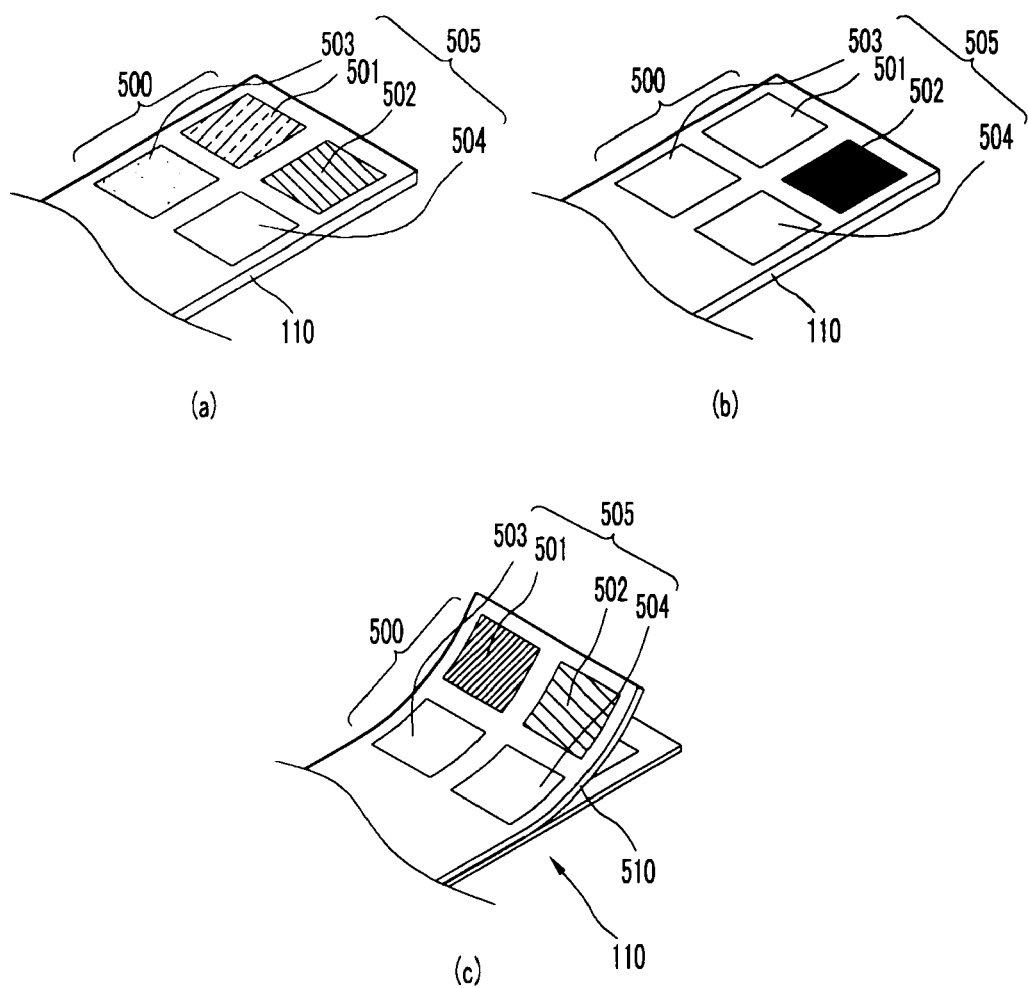
FIG. 10 shows various structures of a biosensor that can be used for a measuring device according to an embodiment of the present invention.
Figure 11:
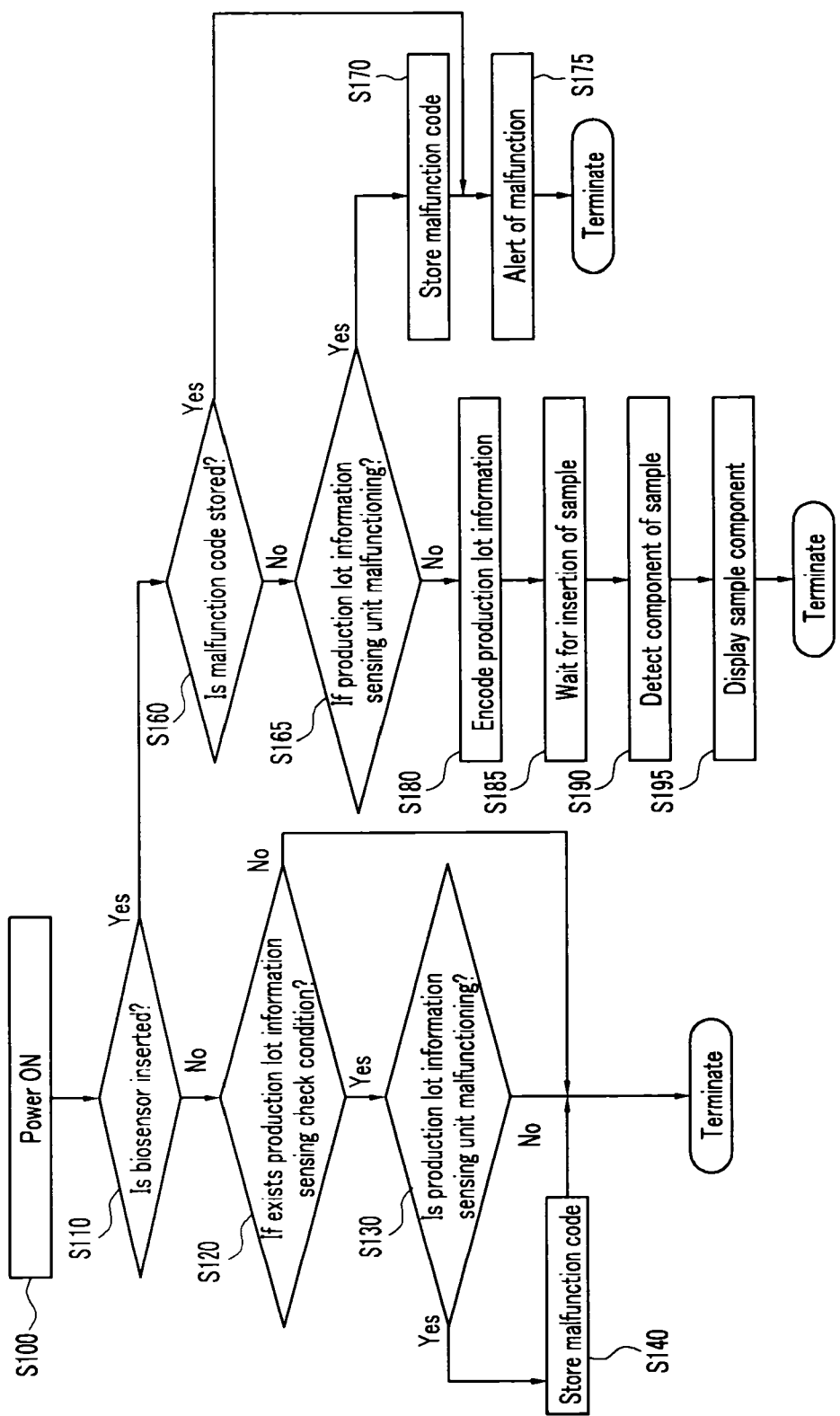
FIG. 11 is a flowchart of a measuring process using a biosensor measuring device according to an embodiment of the present invention.

FIG. 1 exemplarily shows a biosensor measuring device 200 and a biosensor strip 110 that can be used for the biosensor measuring device 200 according to an embodiment of the present invention. FIG. 2 is a block diagram of the biosensor measuring device 200 according to the embodiment of the present invention. Various structures of the biosensor 110 that can be used for the measuring device 200 according to an embodiment of the present invention are shown in FIG. 10.

As shown in FIG. 1 and FIG. 2, a biosensor measuring device 200 according to an embodiment of the present invention includes a production lot information sensing unit 800 that generates a production lot information signal from a production lot information mark 505 marked on the biosensor 110; a measuring module 400 that encodes the production lot information based on the signal from the production lot information sensing unit 800, and uses the encoded production lot information for detecting a specific component (for example, measuring glucose levels in the blood); a display window 460 for displaying a biosensor measuring result of the measuring module 400; and a memory 450 for storing necessary information in operation of the measuring device 200.

The biosensor measuring device 200 is provided with an insertion unit 300 into which the biosensor 110 is inserted, and a connector 700 for connection to an electrode unit of the biosensor 110 and the production lot information sensing unit 800 are installed in the insertion unit 300.

The production lot information sensing unit 800 includes a light emission unit 720 including at least one light emitting body 702, and a detection unit 730 including at least one detector 703 that detects light that is emitted from the light emission unit 720 and passed through a production lot information identification unit 500 of the biosensor 110.

The measuring module 400 includes at least one processor driven by a predetermined program, and the predetermined program may include a series of commands for performing a measuring method according to an exemplary embodiment of the present invention that will be described later.

The biosensor measuring device 200 may be provided with a button 410 in order to be operated by a user.

The electrode unit of the biosensor 110 measured by the electrochemical biosensor measuring device 200 according to an embodiment of the present invention may be formed on one or both of at least two planar insulating plates. That is, (1) a single working electrode and a single auxiliary electrode (or reference electrode) may be formed on the same planer insulating plate, or (2) may be formed on two planar insulating plates facing each other [parallel electrodes; reference: E. K. Bauman et al., Analytical Chemistry, Vol. 37, p 1378, 1965; K. B. Oldham in "Microelectrodes: Theory and Applications," Kluwer Academic Publishers, 1991].

In addition, the electrode unit of the electrochemical biosensor 110 used in the electrochemical biosensor measuring device 200 according to the exemplary embodiment of the present invention may further include a flow sensing electrode that is disposed behind the working electrode and is capable of measuring the fluidity of whole blood samples on a lower planar insulating plate.

Hereinafter, the biosensor 110 will be described in greater detail taking parallel electrodes as an example.

In the case that the electrochemical biosensor 110 used for the electrochemical biosensor measuring device 200 according to the exemplary embodiment of the present invention is formed using the parallel electrodes, the biosensor 110 may have a structure in which the working electrode and the auxiliary electrode are spaced apart from each other by a pressure-adhesive spacer of which the thickness is 50-250 μm, and symmetrically or asymmetrically face each other.

In the spacer, a capillary sample cell of a microliter volume scale is provided for injecting a biosample in a measurement space defined by the working electrode and the auxiliary electrode and retaining the sample therein. The capillary sample cell includes a sample introducing portion and a micro-path.

In the forming of the electrode, the flow sensing electrode in the spacer is preferably placed at a predetermined distance from the working electrode or the auxiliary electrode so that a fluorinated blood having a corpuscle volume of 40% can reach the working electrode (or the auxiliary electrode) along a micro-path of a width of 0.5-2 mm and a height of 50-250 μm within about 600 ms, and more particularly, the flow sensing electrode is placed at a predetermined distance from the working electrode or the auxiliary electrode such that a non-fluorinated sample can reach the electrode along the micro-path within about 300 ms, and still more particularly within about 200 ms.

Functioning to introduce a blood sample into one end of the biosensor 110, the sample-introducing portion is formed in an L shape so as to allow rapid, accurate, and convenient introduction of a blood sample from the fore end of the biosensor 110. The sample introducing portion is structured such that an allowance space is formed in a location at which a sample introducing path and an air vent cross each other. In the present specification, the term "cross" means that the sample-introducing path and the air vent are not arranged parallel to each other but intersect each other at a predetermined point. During measurement, the allowance space helps maintain a constant and accurate volume of the blood sample within the path while discharging excess of the sample through the air vent. Also, the allowance space may be used as a place in which the flow sensing electrode is disposed. When the blood sample is introduced into the sample introducing portion, the blood sample moves to the electrode unit through the micropath.

In the biosensor 110 used in the electrochemical biosensor measuring device 200 according to the exemplary embodiment of the present invention, the reaction reagent layer may be formed by simply applying a reagent solution only to the working electrode or to both the working electrode and the flow sensing electrode. The reaction reagent layer includes an oxidase enzyme such as a glucose oxidase enzyme or a lactate oxidase enzyme, an electron transfer mediator, a water-soluble polymer such as cellulose acetate, polyvinyl alcohol, or polypyrrol, a fatty acid having 4 to 20 carbon atoms as a reagent for reducing a hematocrit effect, and a hydrophilic quaternary ammonium salt.

In the electrochemical biosensor measuring device 200 according to the exemplary embodiment of the present invention, an electrode connection unit that electrically connects the biosensor 110 and the measuring device 200 is designed to be formed on the same plane in which the working electrode and the auxiliary electrode are connected via connection lines. The level of component (e.g., blood glucose) of the sample that is measured by the biosensor 110 of the exemplary embodiment of the present invention from the results of an electrochemical reaction is provided to the measuring device 200 through the electrode connection unit such that the level of the component can be numerically converted into a precise level (e.g., a precise blood glucose level).

The electrochemical biosensor 110 according to the exemplary embodiment of the present invention includes a production lot information identification unit 500. The production lot information identification unit 500 provides calibration curve information about various concentrations of liquid samples that are used for respective production lots at the time of manufacturing the biosensor 110, along with biosensor production lot information, to a user.

The production lot information identification unit 500 may include at least one mark 505 selected from a hue mark, a hole mark, and a light-transmitting film-covered hole mark.

In the electrochemical biosensor measuring device 200 according to the embodiment of the present invention, the production lot information input to the hue mark, the hole mark, or the light-transmitting film-covered hole mark can be encoded by using various methods including an optical method, an imaging method, and an infrared ray (IR) beam method. The encoding principle of the measuring device 200 is described in detail below.

At least two light emitters 702, for example, light emitting diodes, are integrated within a small space in the measuring device 200. The light emitting diodes are three-component light emitting diodes emitting red, blue, and green colors, or four-component light emitting diodes emitting white, red, blue, and green, but are not limited thereto. In addition, an infrared light source that emits infrared rays may be used as the light emitter. By using the light emitted from the light emitting diode or the infrared light source, the information encoded by the hue mark, the hole mark, or the light transmitting film-covered hole mark marked in the production lot information identification unit 500 of the biosensor 110 is detected.

It is not necessary that the hole mark has to imply a mechanical/spatial hole, and the hole mark may be a random mark that indicates opposition of transmission or reflection of light emitted from the light emitter. For example, when the temporary mark is marked with a black color on a white background, this mark can be understood as a hole mark since the black color absorbs light and the white color reflects light.

The hue mark may display information about differences between production lots according to differences in color, brightness, chroma, or images. Further, the hole mark may encode information about differences between production lots as a combination of closed and open holes. As for the light-transmitting film-covered hole mark, its information about differences between production lots can be indicated by varying the degree of transmission of the film covering the hole mark. In this instance, the number of hue marks or hole marks may be set to be within a range of 1 to 10.

Light sensed by the marks is transmitted through the marks or reflected from the marks so that a change in intensity or wavelength occurs in the light. The transmitted or reflected light is detected by a detector 703 (e.g., an optical identifier) placed at a location between the light emitters 702. A change in the intensity and wavelength of light, as detected by the detector 703, is delivered to the measuring module 400 so that the production lot information of the biosensor 110 can be encoded.

The light emitters 702 and the detector 703 may be formed in a separated or integrated structure. In addition, the light emitters 702 and the detector 703 may be formed in the same plane as the marks when they are adapted to detect the light reflected from the hue marks, the hole marks, or the light-transmitting film-covered hole marks, and the detector 703 may be formed in a plane opposite to the light emitter 702 when it is adapted to detect the transmitted light.

With regard to the hue marks, differences in images made by several marks correspond to differences in information about production lots. The images of the marks are detected by an image signal identification device 707 and delivered to the measuring module 400 so that the production lot information of the biosensor 110 can be encoded.

The production lot information identification unit 500, used for the electrochemical biosensor 110 that is used for the electrochemical biosensor measuring device 200 of the present invention is not limited to a parallel type of electrochemical biosensor, and may also be applied to a plane type of electrochemical biosensor that is realized such that the working electrode and the auxiliary electrode are formed in the same plate and are thus operated, and to a differential type of electrochemical biosensor that is realized such that the parallel type of electrochemical biosensor and the plane type of electrochemical biosensor process signals differently.

A connector 700 used in the electrochemical biosensor measuring device 200 according to the exemplary embodiment of the present invention may have a structure in which one or more transmission or reflection path(s) of a light emitter-production lot information identification unit-detector can be realized, thereby encoding the production lot information marked on the biosensor 110.

Figure 3:
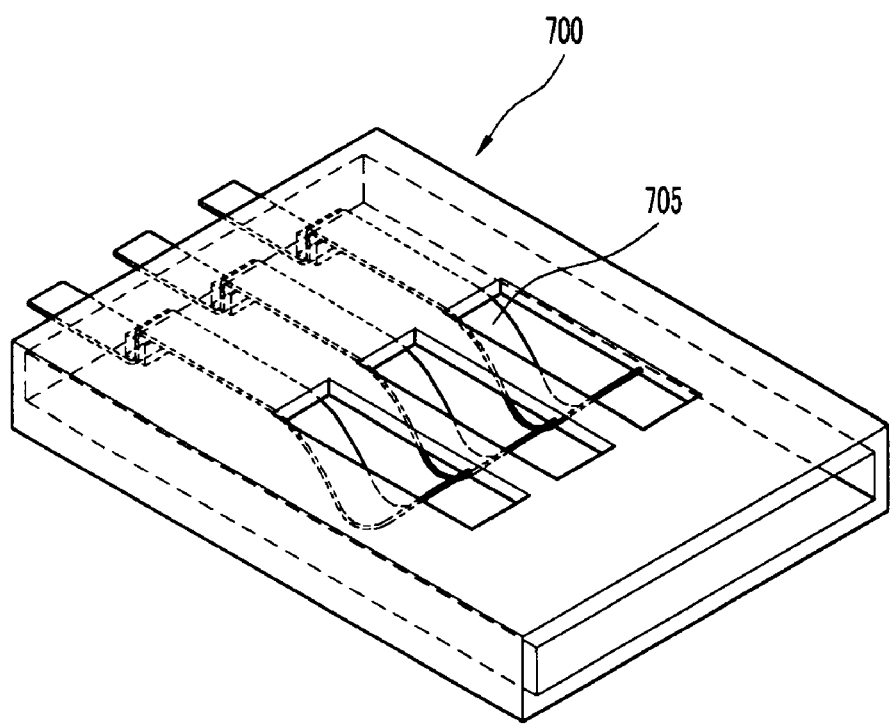
FIG. 3 is a perspective view of a transparent connector in a measuring device according to an embodiment of the present invention.

As shown in FIG. 3, the connector 700, as an example, may be formed of a body made of a transparent material such as transparent acryl or plastic.

Figure 4:
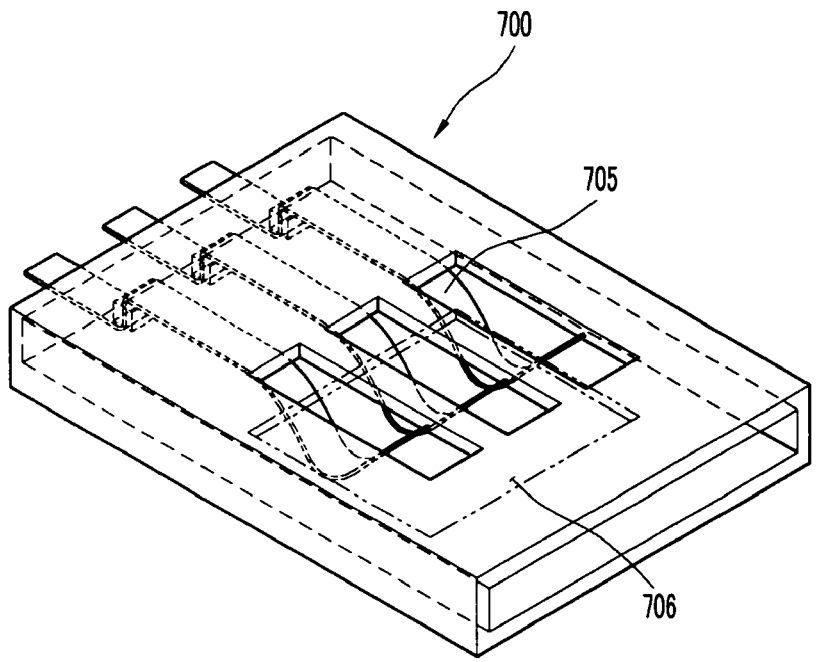
FIG. 4 is a perspective view of a connector provided with a transmission window in one side of the measuring device according to an embodiment of the present invention.

In addition, the connector 700, as shown in FIG. 4, may be provided with a transmission window 706 in one side thereof so that infrared rays transmitted or reflected via the light emitter-production lot information identification unit-detector 700 are passed therethrough. Accordingly, even when the connector 700 is made of an opaque material, or even when the body of the connector 700 is colored, the light radiated by the light emitters 702 can easily reach the production lot information identification unit 500 of the biosensor 110 through the transmission window 706, and thus the production lot information can be encoded.

Figure 5:
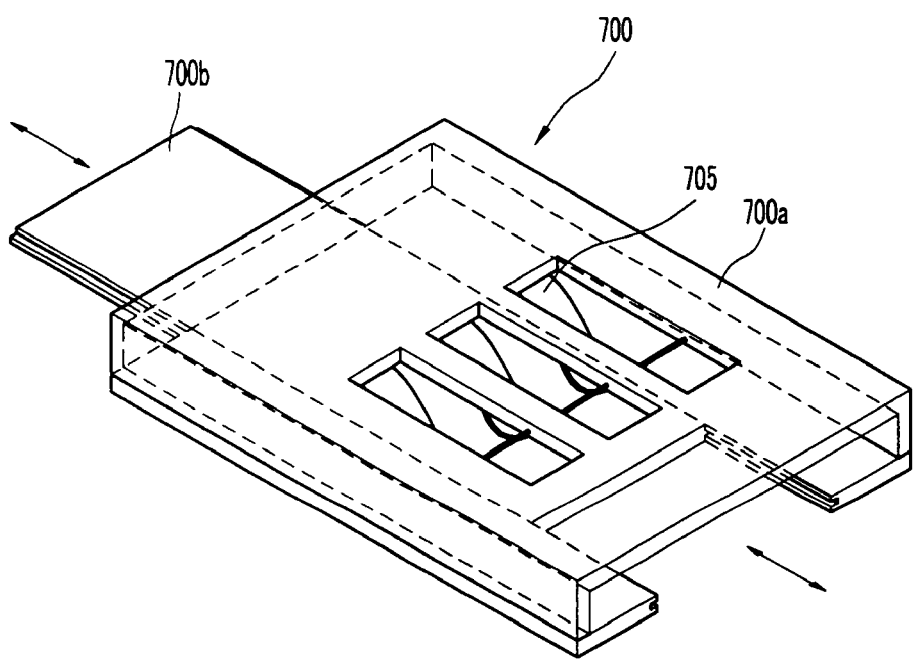
FIG. 5 is a perspective view of a connector formed to have a sliding window in one side of a measuring device according to an embodiment of the present invention.

Furthermore, as shown in FIG. 5, the connector 700 may be manufactured such that one side thereof has a sliding door structure 700b in order to pass the light that is transmitted or reflected via the light emitter-production lot information identification unit-detector, through the connector 700. In further detail, when inserting the biosensor 110 into the connector 700, the sliding door structure 700b of the connector 700 is pushed along with the biosensor 110 in the insertion direction of the biosensor 110, and therefore the path along which the light can reach the production lot information identification unit 500 of the biosensor 110 can be realized. In this case, the sliding door structure 700b may be connected to a device that can manually or automatically remove the biosensor 110, and therefore the biosensor 110 can be easily separated and removed from the biosensor measuring device 200 using the removing device (not shown) after the use of the biosensor 110.

Figure 6:
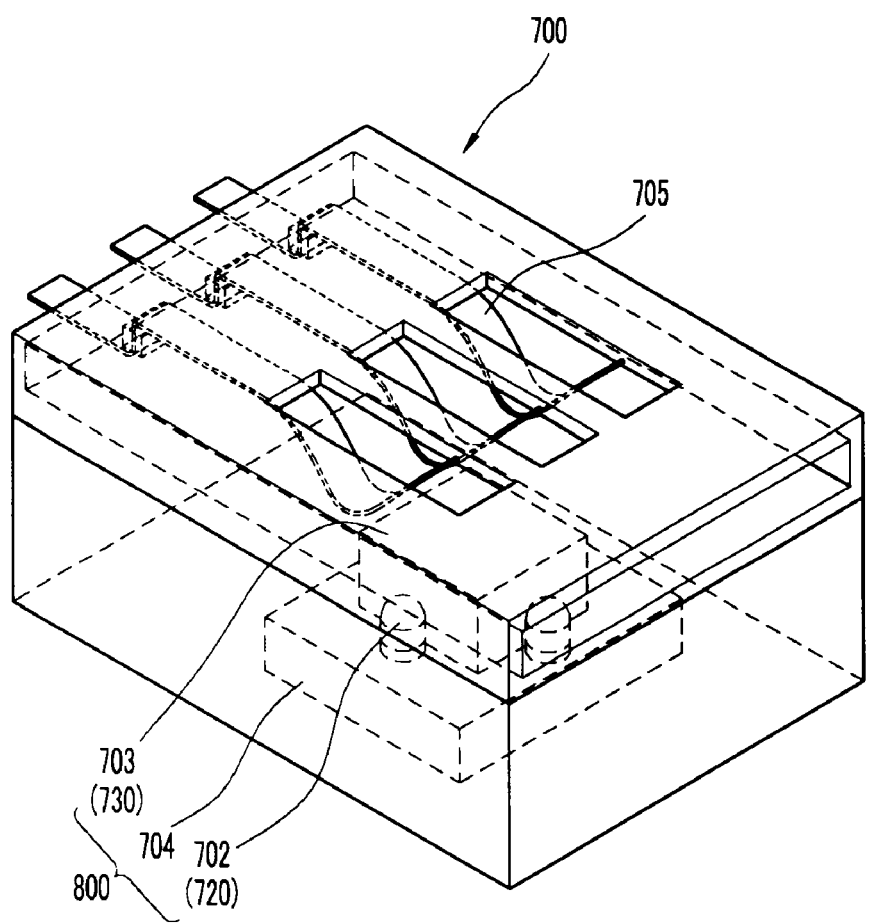
FIG. 6 is a perspective view of a connector having a structure in which a production lot information sensing unit is combined in a measuring device according to an embodiment of the present invention.
Figure 7:
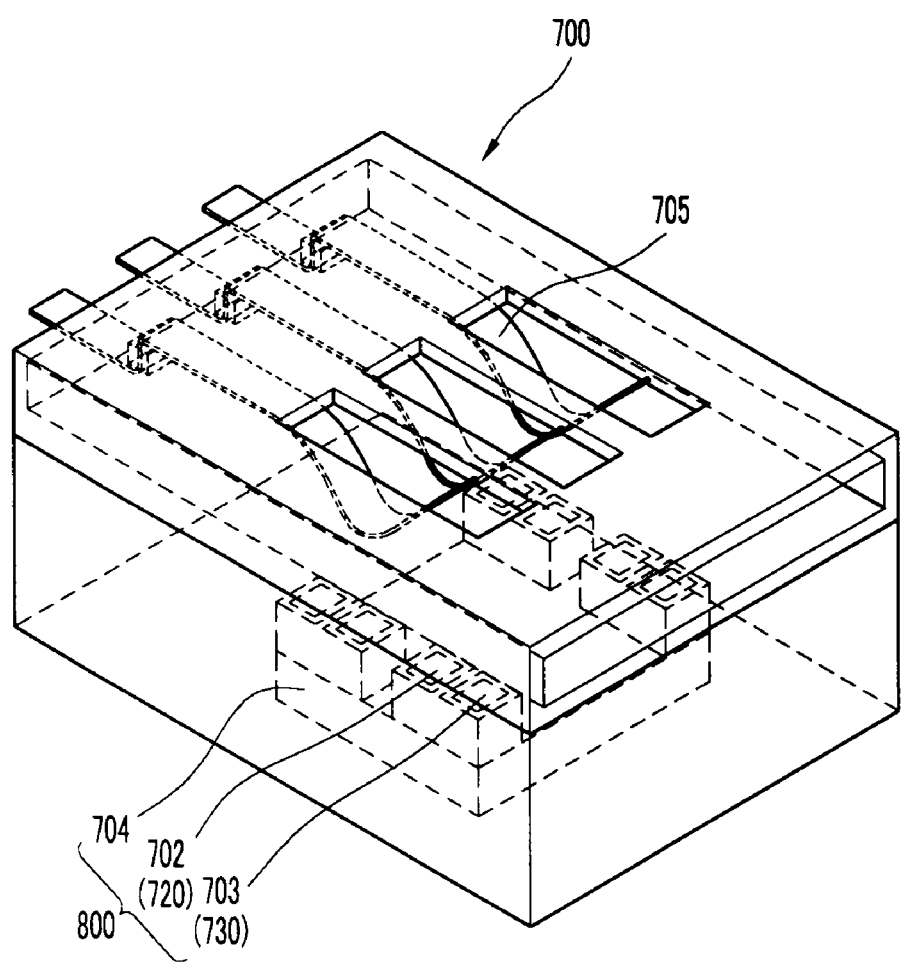
FIG. 7 is a perspective view of a connector having a structure in which a production lot information sensing unit is combined in a measuring device according to an embodiment of the present invention.
Figure 8:
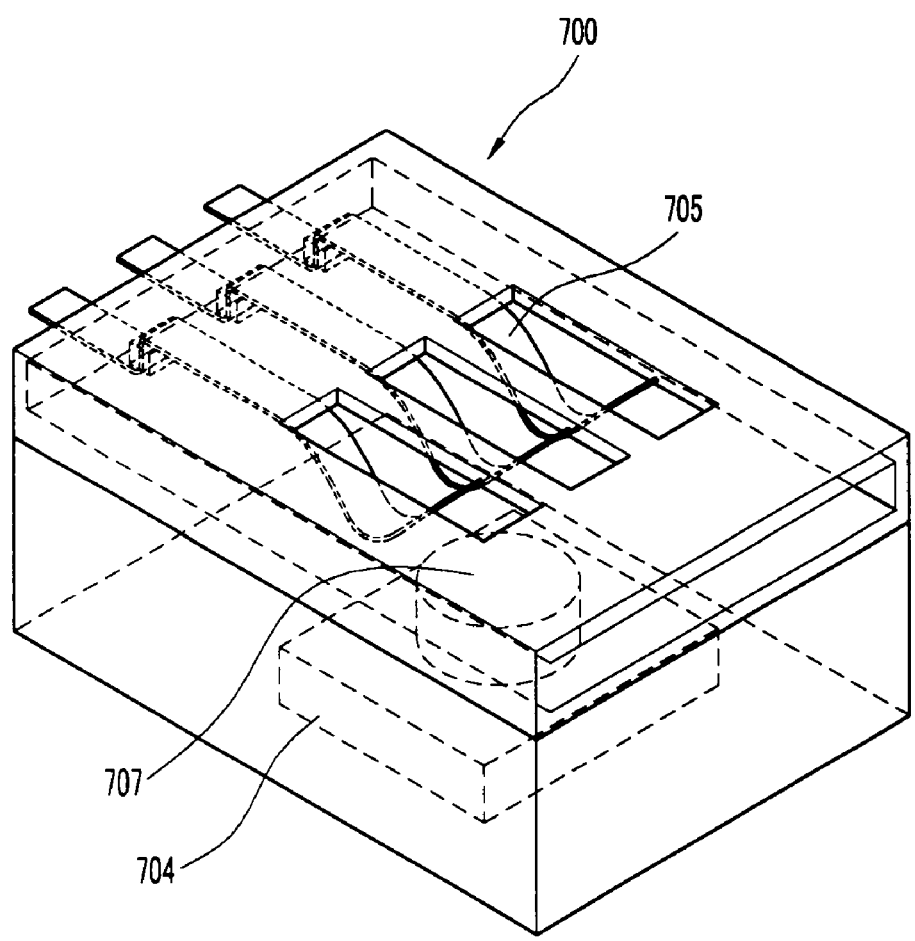
FIG. 8 is a perspective view of a connector having a structure in which an image signal identification device is combined in a measuring device according to an embodiment of the present invention.
Figure 9:
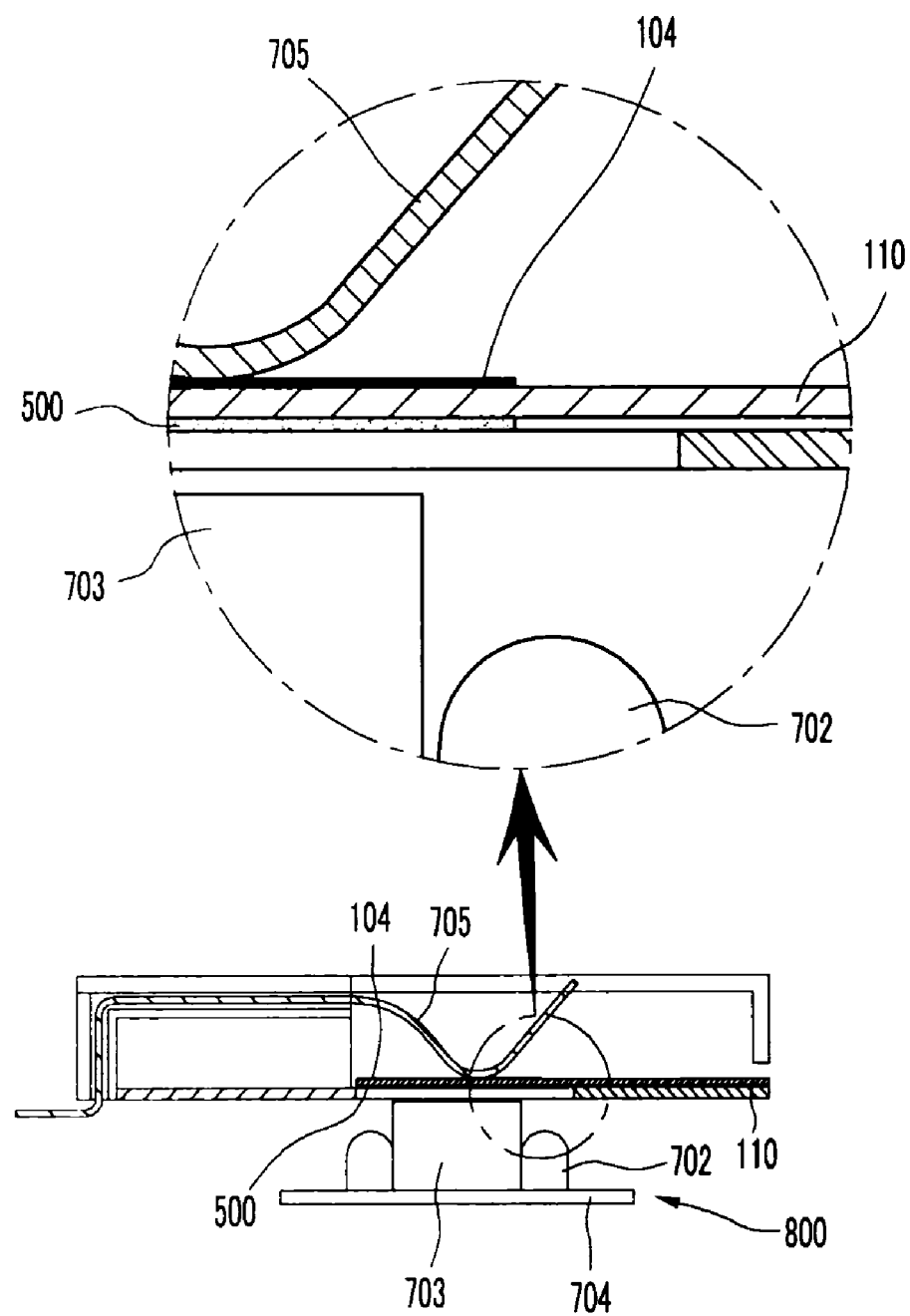
FIG. 9 is a cross-sectional view of insertion of a biosensor to a connector in a measuring device according to an embodiment of the present invention.

In addition, as shown in FIG. 6, FIG. 7, and FIG. 8, the connector 700 may include the light emitters 702, the detector 703, and electrical connection units 705 in an integrated structure within the body thereof. For example, the connector 700 of FIG. 6 employs a three-color diode as a light emitter 702 and an optical identifier as a detector 703 in an integrated structure by which differences in the color, brightness, or chroma of the production lot information identification unit 500 of the biosensor 110 are detected to thereby encode the production lot information. The connector 700 of FIG. 7 employs an infrared light source as a light emitter 702 and an optical identifier as a detector 703 in an integrated structure in order to discriminate the differences in the color, brightness, or chroma of the production lot information identification unit 500 of the biosensor 110, thereby encoding the production lot information. The connector 700 of FIG. 8 employs an image signal identification device 707 as a detector by which the image encoded by the hue mark of the production lot information identification unit 500 is detected so as to encode the production lot information. For example, a charge coupled device (CCD) camera may be used as the image signal identification device.

FIG. 10 shows various structures of the biosensor used for the measuring device according to the embodiment of the present invention.

FIG. 10 exemplarily shows that four production information marks 501, 502, 503, and 504 are included in the production lot information identification unit 500.

First, in (a) of FIG. 10, the production lot information marks 501, 502, 503, and 504 are marked with the hue mark. The hue mark can realize various hues such as color, brightness, chroma, and images. For example, a first mark 501 of (a) of FIG. 1 exhibits dark color, low brightness, low chroma, and massed images, and these color, brightness, chroma, and images become gradually brighter to a second mark 502, a third mark 503, and a fourth mark 504, and the images are less diffused.

In (b) of FIG. 10, the production lot information mark includes hole marks 501, 502, 503, and 504, but the production lot information is displayed according to the number of cases of combinations of open and closed holes. For example, the first, third and fourth hole marks 501, 503, and 504 are in the closed state, and the second hole mark 502 is in the state that light is absorbed and thus a reflection wave is not provided, like a hole. Since the first, second, third, and fourth hole marks 501, 502, 503, and 504 can be interpreted as 16 combinations by using binary codes, a detection unit for recognizing the open and closed state can be very simple.

In (c) of FIG. 10, the production lot information mark includes a hole mark covered by a transmission film 501, and regions having different degrees of transmission are formed in the transmission film 510. Therefore, the detector 703 can detect different light passed through the different regions 501, 502, 503, and 504 respectively having different degrees of transmission so that the production lot information can be encoded by combination thereof (or by intensity of light when only one region is formed).

In the biosensor measuring device 200 according to the exemplary embodiment of the present invention, it may be difficult or uneconomical to construct a system in which a hue or hole mark identification circuit of a photospectrometer system is installed with a circuit and device for measuring the biosensor 110 of an electrochemical system. However, with the recent development of small-sized light emitting devices, detecting devices, and circuit design technologies, a system, the construction of which was considered unfeasible in the past due to incompatibility between constitutional components, can be easily and economically realized in a small circuit space at minimal cost.

For example, conventional devices for reading hue marks using a filter or a prism-type monochromater to determine the wavelength of a light source encounter great spatial limitations and cause problems in the construction of small-sized systems. In the identification of the production lot information, in contrast, the biosensor 110 according to the exemplary embodiment of the present invention can readily identify hue marks and allows the construction of an economical system because it uses small-sized three-component light emitting diodes that simultaneously emit red, blue, and green colors and detects overall variation in the light reflected from or transmitted through the hue marks with a small-sized optical identification device. The advantage of such electrochemical measurement is combined with the advantages of recent small-sized spectral device technologies obtained by the development of technology, and thus a biosensor 110 that is economical and provides precise measurement values can be provided.

A measuring method of the electrochemical biosensor measuring device 200 according to the exemplary embodiment of the present invention will now be described in further detail.

First, power of the measuring device 200 is activated (S100). The power may be turned on by operating the button 410, or may be turned on by inserting the biosensor 110 into the measuring device 200.

Therefore, when the power is turned on, the measuring device 200 determines whether the biosensor 110 is inserted (S110).

When the biosensor 110 is not inserted, the measuring device 200 determines whether to determine if a malfunction of the production lot information sensing unit 800 exists (S120). For the determination, a person of ordinary skill in the art can readily set determination references including determining whether a specific time has been reached every day and whether a predetermined time has passed from the last determination of malfunction of the sensing unit 800.

When it is determined to determine whether the sensing unit 800 malfunctions, the measuring module 400 determines malfunction of the sensing unit 800 based on a sensing value of the sensing unit 800 (S130). A detailed process for determining malfunction of the sensing unit 800 will be described later with reference to FIG. 12.

When the sensing unit 800 malfunctions, a malfunction code is stored in a memory 450 (S140), and a malfunction determining process of the sensing unit 800 is terminated.

When the sensing unit 800 does not malfunction or when it is determined to not determine whether the production lot information sensing unit 800 malfunctions in the step of S120, the malfunction determining process of the sensing unit 800 is terminated.

After termination, the measuring process according to the exemplary embodiment of the present invention is performed again in order to cope with any change such as insertion of the biosensor 110.

When the biosensor 110 is inserted in the step of S110, the measuring module 400 determines whether a malfunction code is stored in the memory 450 (S160).

Figure 12:
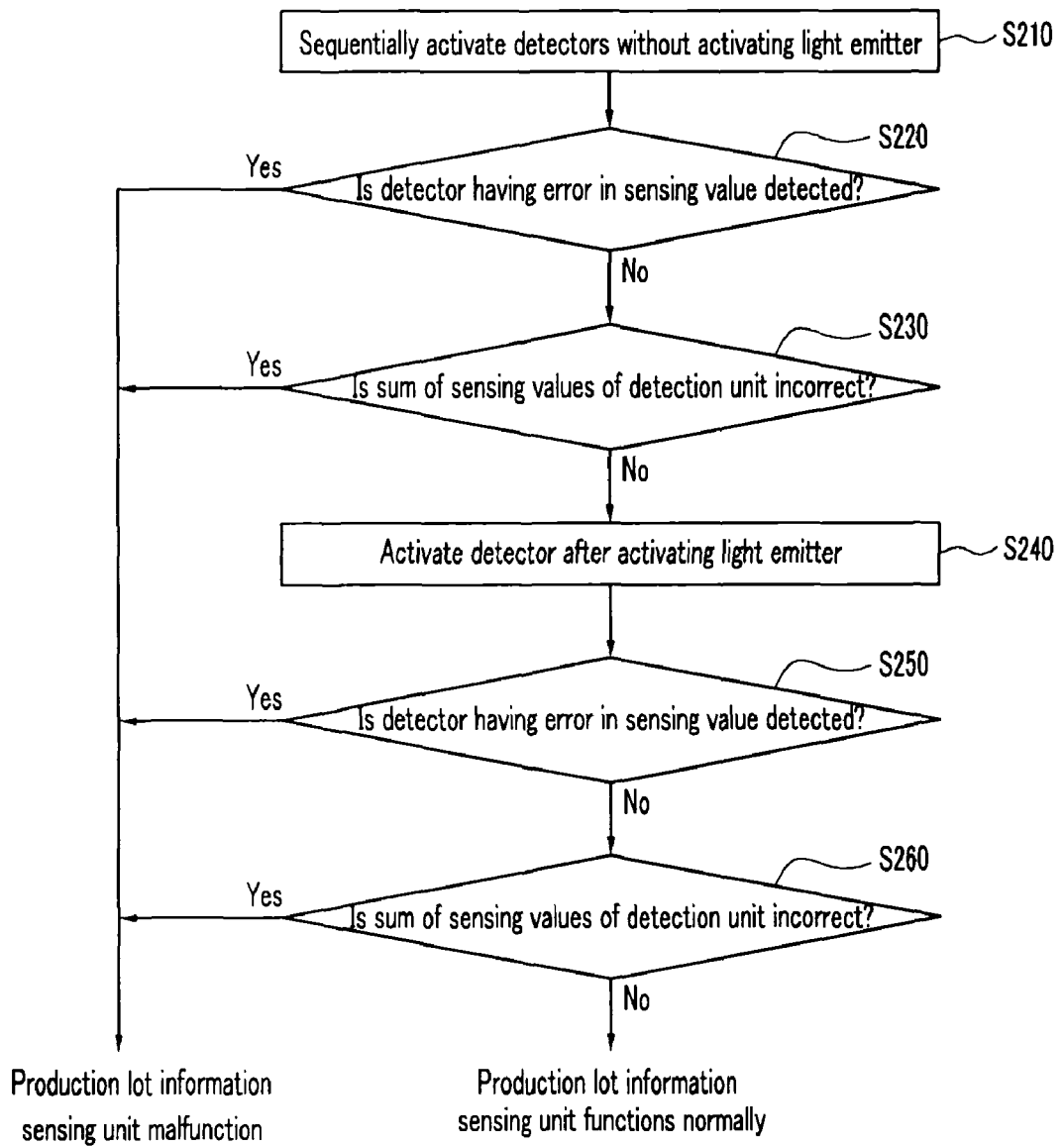
FIG. 12 is a flowchart of a process for determining malfunction of a production lot information sensing unit in a measuring process of a biosensor measuring device according to the present invention.

When the malfunction code is not stored in the memory 450, the measuring module 400 determines whether the sensing unit 800 malfunctions (S165). The determination of the malfunction (S165) can be determined the same as the malfunction determination (S130), as shown in FIG. 12. When the sensing unit 800 malfunctions, the measuring module 400 stores a malfunction code in the memory 450 (S170).

When the malfunction code is stored in the memory 450 or when the sensing unit 800 is determined to be malfunctioning in the step of S165 and thus the malfunction code is stored in the memory 450 (S170), the measuring module 400 transmits an alert message (S175), and the malfunction determining process of the sensing unit 800 is terminated.

When the malfunction code is not stored in the memory 450 and the sensing unit 800 is determined to not be malfunctioning, the measuring module 400 encodes production lot information of the biosensor through the sensing unit 800 (S180).

In this case, the encoding of the production lot information may be realized by encoding at least one of a hue mark, a hole mark, and a light-transmitting film-covered hole mark that are displayed on the biosensor 110.

The hue mark may display the information about differences between production lots by differences in the color, brightness, or chroma of a plurality of color images. The hole mark may encode the information about differences between production lots in the form of a combination of holes that are independently open or closed, and the light-transmitting film-covered hole mark may encode the information about differences between production lots by varying the degree of transmission of films covering a plurality of open holes. In this case, the number of hue marks or hole marks may be set to be within a range of 1 to 10.

Encoding of the production lot information can be achieved as follows.

For example, the hue mark, the hole mark, or the light-transmitting film-covered hole mark of the production lot information identification unit 500 is detected by sequentially emitting light from three-component light emitting diodes of red, blue, and green or four-component light emitting diodes of white, red, blue, and green. Variations in wavelength, color, brightness, and chroma depending on the degrees of reflection or transmission of detected light are detected by an optical identification device so that the production lot information can be encoded.

In another example, the hue mark, the hole mark, or the light-transmitting film-covered hole mark of the production lot information identification unit 500 is detected by radiating infrared rays selected from one or more infrared ray sources that can emit infrared rays. Variations in wavelength, color, brightness, and chroma depending on the degrees of reflection or transmission of detected light are detected by an optical identification device so that the production lot information can be encoded.

In another example, image signals are detected from the hue marks of the production lot information identification unit 500 and differences of visualized images are detected by a video signal identifying device, thereby encoding the production lot information.

The measuring module 400 having encoded the production lot information of the biosensor 110 waits for a sample of an object to be measured to be inserted into the biosensor 110 (S185), and if the sample is inserted, the measuring module 400 detects a component such as blood glucose of the inserted sample (S190). If the sample has already been inserted into the biosensor 110, the detection step (S190) is directly performed. Various processes for detecting the component of the sample inserted into the biosensor 110 are known to a person of ordinary skill in the art, and therefore a further description will not be provided.

When the component of the sample is detect, the detected component of the sample is displayed through the display window 460.

Hereinafter, the processes (S130 and S165) for determining malfunction of the sensing unit 800 determined by the biosensor measuring device 200 according to the exemplary embodiment of the present invention will be described in further detail with reference to FIG. 12. In the exemplary embodiment of the present invention, malfunction of both the detection unit 730 and the light emission unit 720 can be determined.

First, in order to determine malfunction of the detection unit 730, the measuring module 400 measures a sensing value from the detection unit 730 in the deactivated state of the light emission unit 720 (S210), and determines whether the detection unit 730 malfunctions based on the measured sensing value.

When the detection unit 730 includes a plurality of detectors 703, malfunction of each detector 703 can be determined on the basis of a sensing value of the corresponding detector 703, which is obtained by sequentially activating the plurality of detectors 703. The malfunction of each detector 703 can be determined based on whether the sensing value of each detector 703 is in excess of a first predetermined range (S220). The first predetermined range can be set by a person of ordinary skill in the art with reference to a specification of an adapted detector 703.

In addition, in the exemplary embodiment of the present invention, the malfunction of the sensing unit 800 is determined in consideration of an operation result of the sensing values of the plurality of detectors 703 (S230). Operation of the sensing values, as an example, may be a sum of a sequentially obtained sensing value of each detector 703, but it should be understood that the scope of the present invention is not limited thereto. Malfunction of the detection unit 730 can be determined by another function (e.g., product operation) that is operated by all of the sensing values of the respective detectors 703. In another example, the malfunction of the detection unit 730 can be determined by using sensing values that are obtained by simultaneously activating the plurality of detectors 703. It may be determined that the detection unit 730 malfunctions when an operation result of each sensing value is in excess of a second predetermined range, and the second predetermined range can be readily set by a person of ordinary skill in the art with reference to specifications of the respective detectors 703 and operation rules of the sensing values.

When the detection unit 730 is determined to be malfunctioning by the above determination, the sensing unit 800 is determined to be malfunctioning and a malfunction determining process of the sensing unit 800 is terminated.

When the detection unit 730 does not malfunction, malfunction of the light emission unit 702 is determined (S240 to S260). The light emission unit 720 is activated and a sensing value obtained from the detection unit 730 is measured (S240), and then malfunction of the light emission unit 702 may be determined on the basis of the measured sensing value.

When the light emission unit 702 includes a plurality of light emitters 702, the respective light emitters 702 are activated and malfunction of each light emitter 702 can be determined on the basis of a sensing value of a detector 703 that corresponds to an activated light emitter 702. Malfunction of each light emitter 702 can be determined based on whether the sensing value of the detector 703 corresponding to the activated light emitter 702 is in excess of a third predetermined range (S250). The third predetermined range may be readily set by a person of ordinary skill in the art with reference to specifications of the light emitter 702 and the detector 703.

In addition, in the exemplary embodiment of the present invention, the malfunction of the sensing unit 800 is determined in consideration of operation results of the sensing values of the respective detectors 703 according to activation of the plurality of the light emitters 702 (S260). Operation of the sensing values, as an example, may be a sum of the sensing values of the respective detectors 703 according to sequential activation of the plurality of light emitters 702, but it should be understood that the scope of the present invention is not limited thereto. Malfunction of the detection unit 730 can be determined by another function (e.g., product operation) that is operated by all of the sensing values of the respective detectors 703. In another example, the malfunction of the light emission unit 720 can be determined by using sensing values that are obtained by simultaneously activating the plurality of light emitters 702. It may be determined that the light emission unit 720 malfunctions when an operation result of each sensing value is in excess of a fourth predetermined range, and the fourth predetermined range can be readily set by a person of ordinary skill in the art with reference to specifications of the respective light emitters 702 and the detectors 703 and operation rules of the sensing values.

When the light emission unit 720 is determined to be malfunctioning by the above determination, the sensing unit 800 is determined to be malfunctioning and a malfunction determining process of the sensing unit 800 is terminated.

When both of the detection unit 730 and the light emission unit 720 are determined to be normally functioning, the sensing unit 800 is determined to be normally functioning and the malfunction determining process of the sensing unit 800 is terminated.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

What is claimed is:

1. A biosensor measuring method for detecting a target component in biological samples using a biosensor encoded with product lot information and the product lot information sensing unit having light emitter/detector pairs by irradiating on the product lot information markings with the light emitted from a bank of light emitters and by reading the transmitted or reflected lights from the product lot information markings with the detectors paired with the light emitters, the method comprising:

checking malfunction of the production lot information sensing unit;
alerting the malfunction in the product lot information sensing unit;
decoding the production lot information read through the production lot information sensing unit when the production lot information sensing unit normally operates; and
analytically determining a target component in a sample from the response of the biosensor strip in combination with the decoded production lot information.

2. The biosensor measuring method of claim 1, wherein the checking of malfunction in the production lot information sensing unit comprises:
determining malfunction of the detection unit; and
determining malfunction of the light emission unit, and
the production lot information sensing unit is determined to be malfunctioning if any of the detection unit and the light emission unit malfunctions.

3. The biosensor measuring method of claim 2, wherein the determination of malfunction in the detection unit is based on a sensing value from the detection unit while the paired light emission unit is off.

4. The biosensor measuring method of claim 2, wherein the detection unit comprises a plurality of detectors and the malfunction in detection unit is determined by sequentially activating each detector in the pluarality of detectors and reading the light-off sensing value of each detector.

5. The biosensor measuring method of claim 2, wherein the detection unit comprises a plurality of detectors and the malfunction in the detection unit is determined by respective sensing values read from the plurality of detectors and the values obtained from the mathematical operation of the sensing values of the plurality of detectors.

6. The biosensor measuring method of claim 2, wherein the malfunction in detection unit is determined when the biosensor strip is placed into the device unit where the production lot sensing unit can be activated and the biosensor strip measurement sequence begins.

7. The biosensor measuring method of claim 2, wherein the malfunction in the detection unit is determined without biosensor strip, the result of malfunction determination is recorded in a memory of biosensor measuring device, and the biosensor measuring device alerts the malfunction in the production lot information sensing unit.

8. The biosensor measuring method of claim 2, wherein the malfunction in the light emission unit is determined when the detection unit is determined to be normally functioning.

9. The biosensor measuring method of claim 8, wherein the light emission unit comprises a plurality of light emitters, and the malfunction in the light emission unit is determined by sequentially activating the plurality of light emitters and reading the light-on sensing value of each detector paired with the corresponding emitter.

10. The biosensor measuring method of claim 8, wherein the light emission unit comprises a plurality of light emitters, and the malfunction in the light emission unit is determined by the light-on sensing values of respective detectors when the plurality of light emitters are sequentially activated and the values obtained from the mathematical operation of the light-on sensing values of a plurality of detectors.

11. The biosensor measuring method of claim 1, wherein at least one production lot information mark comprises a hue mark, and the decoding of the production lot information is based on a difference in light absorption or reflection, color, brightness, chroma, or an image of the mark.

12. The biosensor measuring method of claim 1, wherein the at least one production lot information comprises a hole mark, and the decoding of the production lot information is based on determining differences in a combination of a plurality of open and closed holes.

13. The biosensor measuring method of claim 1, wherein the at least one production lot information mark comprises a light-transmitting film-covered hole mark, and the decoding of the production lot information is made by the degree of transmission through films covering the holes.

14. The biosensor measuring method of any one of claim 1 to claim 10, wherein the light emitter is formed of three-component light emitting diodes that emit red, green, and blue colors, four-component light emitting diodes that emit white, red, green, and blue colors, or an infrared ray source that emits infrared rays.

15. A biosensor measuring device for detecting a component of a sample through a biosensor strip having a production lot information identification unit that includes at least one production lot information mark, the biosensor measuring device comprising:
   a production lot information sensing unit including a plurarality of paired light emitters and detectors that reads a production lot information by emitting the light onto and detecting the absorbed or reflected light from the production lot information identification unit; and
   a biosensor strip measuring module that decodes the production lot information and uses the decoded production lot information for analytical determination of a target component in samples,
   wherein the measuring module comprises at least one processor that is activated by a predetermined program, and the predetermined program comprises a series of commands for performing the measuring method of any one of claim 1 to claim 10.

16. The biosensor measuring device of claim 15, wherein the at least one production lot information comprises a hue mark, and the decoding of the production lot information is based on a difference in at least one of light absorption or reflection, color, brightness, chroma, and an image of the hue mark.

17. The biosensor measuring device of claim 15, wherein the at least one production lot information comprises a hole mark, and the decoding of the production lot information is performed by differences in a combination of a plurality of open and closed holes.

18. The biosensor measuring device of claim 15, wherein the at least one production lot information comprises a light-transmitting film-covered hole mark, and the decoding of the production lot information is made by the degree of transmission through films covering the hole mark.

19. The biosensor measuring device of claim 15, wherein the light emitter is formed of three-component light emitting diodes that emit red, green, and blue colors, four-components light emitting diodes that emit white, red, green, and blue colors, or an infrared ray source that emits infrared rays.

* * * * *